United States Patent
Grundei

(10) Patent No.: US 6,709,466 B1
(45) Date of Patent: Mar. 23, 2004

(54) THIGH STUMP ENDOPROSTHESIS FOR AN EXOPROSTHETIC TREATMENT

(75) Inventor: Hans Grundei, Lübeck (DE)

(73) Assignee: Eska Implants GmbH & Co. (DE)

( * ) Notice: Subject to any disclaimer, the term of this patent is extended or adjusted under 35 U.S.C. 154(b) by 0 days.

(21) Appl. No.: 09/913,036

(22) PCT Filed: May 20, 2000

(86) PCT No.: PCT/EP00/04552

§ 371 (c)(1), (2), (4) Date: Aug. 8, 2001

(87) PCT Pub. No.: WO01/05335

PCT Pub. Date: Jan. 25, 2001

(30) Foreign Application Priority Data

Jul. 14, 1999 (DE) .......................................... 199 32 388

(51) Int. Cl.⁷ ................................. A61F 2/60; A61F 2/78
(52) U.S. Cl. ............................................................ 623/32
(58) Field of Search ............................. 623/32, 38, 53, 623/27, 28, 33, 39, 43, 46, 30, 31, 60, 58, 408

(56) References Cited

U.S. PATENT DOCUMENTS

| | | | |
|---|---|---|---|
| 3,947,897 A | | 4/1976 | Owens |
| 4,143,426 A | * | 3/1979 | Hall et al. ..................... 623/53 |
| 4,158,895 A | | 6/1979 | Reswick et al. |
| 5,041,137 A | * | 8/1991 | Nemoshkalov .......... 623/16.11 |
| 5,549,682 A | | 8/1996 | Roy |
| 5,766,251 A | | 6/1998 | Koshino |
| 6,425,925 B1 | * | 7/2002 | Grundei ........................ 623/32 |
| 6,482,238 B1 | * | 11/2002 | Grundei ........................ 623/32 |
| 6,485,522 B1 | * | 11/2002 | Grundei ........................ 623/38 |

FOREIGN PATENT DOCUMENTS

| | | | | |
|---|---|---|---|---|
| DE | 31 25 268 | | 1/1983 | |
| DE | 42 08 247 | | 3/1992 | |
| DE | 43 38 746 | | 5/1995 | |
| DE | 19627994 | * | 1/1997 | .................. 623/32 |
| DE | 196 30 298 | | 1/1998 | |
| DE | 198 26 638 | | 12/1999 | |
| DE | 198 57 907 | | 4/2000 | |
| DE | 19931882 C1 | * | 5/2001 | .................. 623/32 |
| EP | 0 577 178 | | 1/1994 | |
| EP | 0 639 351 | | 2/1995 | |
| GB | 2 231 271 | | 11/1990 | |
| JP | 01085645 A | * | 3/1989 | .................. 623/32 |
| WO | WO 91 07932 | | 6/1991 | |
| WO | WO 99/65426 A1 | * | 12/1999 | .................. 623/32 |
| WO | WO02/13729 A1 | * | 2/2002 | .................. 623/32 |
| WO | WO 02/13733 A2 | * | 2/2002 | .................. 623/32 |

\* cited by examiner

Primary Examiner—Corrine McDermott
Assistant Examiner—Alvin Stewart
(74) Attorney, Agent, or Firm—Cantor Colburn LLP

(57) ABSTRACT

The invention relates to a thigh stump endoprosthesis for an exoprosthetic treatment of a patient whose leg has been amputated in the thigh area, whereby the thigh stump can be pulled into a shaft to which the replica of a lower leg part and foot part of the prosthesis is attached. The inventive prosthesis includes a proximal shaft part which can be inserted inside a femur stump, whereby the shaft part is at least partially covered by an open-mesh three-dimensional spatial network structure, and includes a conical adapter on the distal end thereof. A condyle replacement which re-creates the shape of natural condyles of a knee joint can be coupled to the shaft part by means of said adapter. A cuneiform support can be joined to the condyle replacement with a wedge angle α which restores the valgity of the leg.

8 Claims, 1 Drawing Sheet

THIGH STUMP ENDOPROSTHESIS FOR AN EXOPROSTHETIC TREATMENT

FIELD OF THE INVENTION

This invention concerns a femoral stump endoprosthesis for exoprosthetic care of a patient whose leg has been amputated in the femoral region. The femoral stump can be drawn into a shaft to which the simulation of a knee, lower leg and foot part of the prosthesis is connected. The endoprosthesis has a proximal post part, which can be set in a femoral stump, whereby the post part is covered, at least partly, with an open-mesh, 3D spatial network structure and has a conical adapter on its distal end, by means of which a condyle replacement, which simulates the shape of the natural condyle of a knee joint, is attached to the post part.

DESCRIPTION OF THE RELATED ART

An implant is known (U.S. Pat. No. 5,766,251) from the field of surgery that is designed as a wedge-shaped equalizer that permits corrections in the angle of valgity, for example. The wedge-shaped implant is used, inter alia, in the joint area of the tibia, whereby the tibia plateau is lifted on one side according to the angle of inclination of the wedge-shaped implant. However, this publication gives no indication of the implant being used on a patient whose leg has been amputated.

SUMMARY OF THE INVENTION

According to the invention, a wedge-shaped support is connected to the condyle replacement and reproduces the natural valgity, i.e., the angle of the femoral stump in the medial direction. This makes the distribution of forces feel like the distribution of forces in a healthy leg. It means that the wedge can produce parallelism between the bottom of the wedge and the smooth surfaces of an artificial knee joint, to a great extent maintaining the natural CCD angle. This equalizes the stress along the axis of the prosthesis.

In another preferred embodiment, the wedge angle ranges between 5° and 9°. The 5° angles are preferably used on male patients, and the 9° maximally on female patients.

The support is preferably connected to the shock-absorbing layer of the femoral stump endoprosthesis.

Making the support out of a shock-absorbing cushion, so that stresses are not introduced directly into the femoral stump, is especially preferred. For this purpose, the support is preferably made of silicon.

BRIEF DESCRIPTION OF THE DRAWINGS

The invention will be described in greater detail using an example of an embodiment and the single FIGURE in the drawing.

The single FIGURE is a schematic view of a thigh stump 1 with a femoral stump endoprosthesis implanted in the femoral stump 5. The thigh stump 1 is drawn into a shaft 2, which is connected to an artificial lower leg 3 of the prosthesis.

DETAILED DESCRIPTION OF A PREFERRED EMBODIMENT

Figure 1:
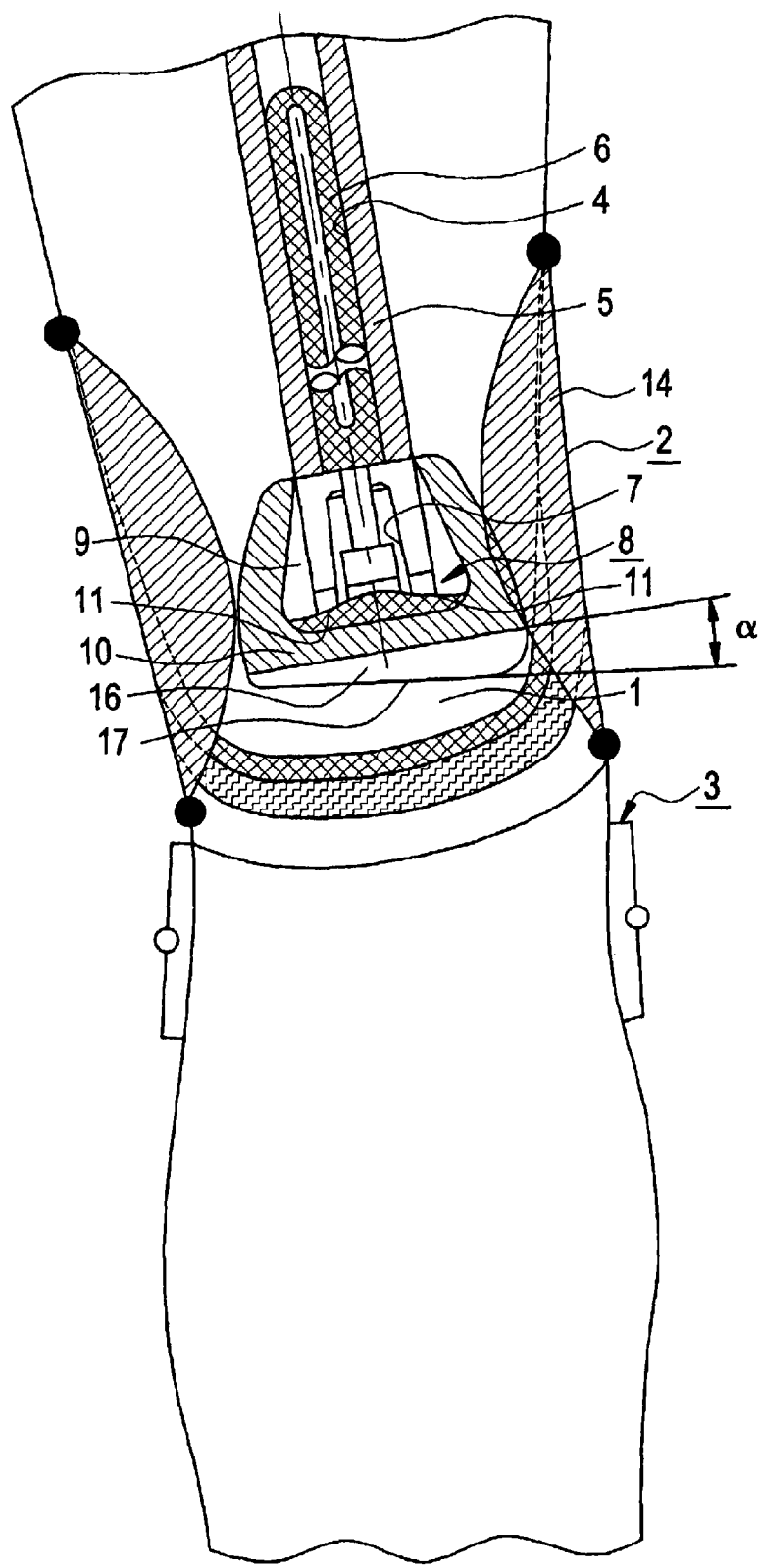

An intramedullary post 4 forms the proximal part of the post, which is set into the medullary space of the femoral stump. The surface of the post part 4 has an open-mesh, 3D spatial network structure 6, through which the bone trabeculae can grow, so that after a certain healing phase, which concerns the substrate flow, the post part 4 has become an almost integral part of the natural bone.

On the distal side, a conical adapter 7 is attached to the post part 4. This conical adapter 7 is used to attach the condyle replacement 8 to the post part 4 on the distal side.

The condyle replacement 8 is designed to simulate the shape 11 of the natural condyle of a knee joint.

The condyle replacement 8 here is coated with a shock-absorbing layer 10 of silicon.

The support 16 is connected to the condyle replacement 8 and to the covering, shock-absorbing layer. The support 16 is designed to be wedge-shaped and has a wedge angle to the horizontal ranging from $5°<\alpha<9°$.

The support 16 here is composed of a damping cushion and in the example of embodiment shown, thus supports the absorption of shock stresses on the artificial lower leg 3. The wedge angle $\alpha$ of the support 16 is adapted to the individual patient, so that the bottom 17 of the support 16 runs basically parallel to the plane of the sliding track of the artificial condyle of an attached artificial knee joint.

This distributes the stresses equally over the whole prosthesis to a large extent.

What is claimed is:

1. A thigh stump endoprosthesis for a thigh stump having a femur stump, the thigh stump is disposed in a shaft, and an artificial lower leg is connected to the shaft, the endoprosthesis comprising:
   a stem part having a first end and a second end, said first end is set into the femur stump;
   an open-mesh, three-dimensional lattice covering at least partially the stem part;
   a conical adapter on the second end of the stem part;
   a condyle replacement modeled to the shape of natural condyles of a knee joint and coupled to the stem part; and
   a wedge-shaped base connected to the condyle replacement.

2. The thigh stump endoprosthesis according to claim 1, wherein a wedge angle $\alpha$ of the base is in the range $5°<\alpha<9°$.

3. The thigh stump endoprosthesis according to claim 2, wherein the base is connected to a shock-absorbing layer.

4. The thigh stump endoprosthesis according to claim 2, wherein the base comprises a shock-absorbing cushion.

5. The thigh stump endoprosthesis according to claim 1, wherein the base is connected to a shock-absorbing layer.

6. The thigh stump endoprosthesis according to claim 5, wherein the base comprises a shock-absorbing cushion.

7. The thigh stump endoprosthesis according to claim 1, wherein the base comprises a shock-absorbing cushion.

8. The thigh stump endoprosthesis according to claim 1, wherein the base comprises silicone.

* * * * *